United States Patent
Gonzalez et al.

(10) Patent No.: US 11,709,119 B2
(45) Date of Patent: Jul. 25, 2023

(54) DETERMINING THE RHEOLOGICAL PROPERTIES OF A FLUID THROUGH A NON-LINEAR RESPONSE

(71) Applicant: Saudi Arabian Oil Company, Dhahran (SA)

(72) Inventors: Miguel Gonzalez, Houston, TX (US); Max Deffenbaugh, Fulshear, TX (US); Hyongsu Baek, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 151 days.

(21) Appl. No.: 17/142,691

(22) Filed: Jan. 6, 2021

(65) Prior Publication Data

US 2021/0208046 A1  Jul. 8, 2021

Related U.S. Application Data

(60) Provisional application No. 62/957,556, filed on Jan. 6, 2020.

(51) Int. Cl.
*G01N 11/10* (2006.01)
*G01N 33/28* (2006.01)
*G01N 11/00* (2006.01)

(52) U.S. Cl.
CPC ............. *G01N 11/10* (2013.01); *G01N 33/28* (2013.01); *G01N 2011/004* (2013.01); *G01N 2011/0033* (2013.01)

(58) Field of Classification Search
None
See application file for complete search history.

(56) References Cited

U.S. PATENT DOCUMENTS

| | | | |
|---|---|---|---|
| 4,754,640 | A | 7/1988 | Fitzgerald et al. |
| 5,177,997 | A | 1/1993 | Maciejewski |
| 2004/0236512 | A1 | 11/2004 | DiFoggio et al. |
| 2010/0191110 | A1 | 7/2010 | Insana et al. |
| 2010/0241407 | A1 | 9/2010 | Hsu et al. |
| 2013/0192349 | A1 | 8/2013 | Ramkumar et al. |
| 2015/0094964 | A1 | 4/2015 | Kuroda et al. |

(Continued)

FOREIGN PATENT DOCUMENTS

| | | |
|---|---|---|
| DE | 4419684 | 12/1995 |
| RU | 2025747 | 12/1994 |
| WO | 2014/049698 | 4/2014 |

OTHER PUBLICATIONS

PCT International Search Report and Written Opinion in International Appln. No. PCT/US2021/012267, dated Apr. 7, 2021, 15 pages.

*Primary Examiner* — Paul M. West
*Assistant Examiner* — Mark A Shabman
(74) *Attorney, Agent, or Firm* — Fish & Richardson P.C.

(57) ABSTRACT

Techniques for determining rheological properties of a fluid include actuating a resonator disposed in a volume that contains a fluid sample to operate the resonator in the fluid sample at a predetermined actuation scheme; measuring at least one characteristic of the resonator based on the operation of the resonator in the fluid sample; comparing the at least one measured characteristic to a rheological model that associates characteristics of the fluid sample to one or more rheological properties; and based on the comparison, determining one or more rheological properties of the fluid sample.

23 Claims, 7 Drawing Sheets

(56) References Cited

U.S. PATENT DOCUMENTS

2016/0138964 A1    5/2016  Brengartner et al.
2016/0223456 A1*  8/2016  Urey .................. G01N 21/1702
2018/0313735 A1*  11/2018  Gallagher ............ G01N 11/162
2019/0226900 A1    7/2019  Brengartner et al.

* cited by examiner

DETERMINING THE RHEOLOGICAL PROPERTIES OF A FLUID THROUGH A NON-LINEAR RESPONSE

CROSS-REFERENCE TO RELATED APPLICATION

This application claims priority under 35 U.S.C. § 119 to U.S. Provisional Patent Application Ser. No. 62/957,556, filed on Jan. 6, 2020, the entire contents of which are incorporated by reference herein.

TECHNICAL FIELD

The present disclosure relates to systems and methods for determining rheological properties of a fluid and, more particularly, determining rheological properties of a fluid used in hydrocarbon exploration and production through a non-linear response of a mechanical resonator.

BACKGROUND

The oil industry uses fluids (for example, non-Newtonian fluids) for the drilling, hydraulic fracturing, and production stimulation of subterranean wells. Chemical industries produce petroleum-derived products in refining and chemical production process from such produced hydrocarbon fluids. Contamination, damage to fluids, or changes in the quality of products can manifest as a change in the rheological properties of fluids used in these processes. In some cases, it may be important for fluids to remain within the design envelope of rheological properties.

SUMMARY

In a general implementation, a method for determining rheological properties of a fluid includes actuating a resonator disposed in a volume that contains a fluid sample to operate the resonator in the fluid sample at a predetermined actuation scheme; measuring at least one characteristic of the resonator based on the operation of the resonator in the fluid sample; comparing the at least one measured characteristic to a rheological model that associates characteristics of the fluid sample to one or more rheological properties; and based on the comparison, determining one or more rheological properties of the fluid sample.

In an aspect combinable with the general implementation, the resonator includes a mechanical resonator.

In another aspect combinable with any one of the previous aspects, the mechanical resonator includes a piezoelectric crystal, a MEMS device, or a tuning fork.

In another aspect combinable with any one of the previous aspects, actuating the resonator includes actuating motion on the resonator through one or more signals to induce harmonic or anharmonic motion.

In another aspect combinable with any one of the previous aspects, the one or more signals includes one or more capacitive, piezoelectric, magnetic, or optical signals.

Another aspect combinable with any one of the previous aspects further includes actuating the resonator with an actuation protocol that actuates the resonator in at least one of a steady state motion or a time-dependent motion.

In another aspect combinable with any one of the previous aspects, the time-dependent motion includes at least one sequence of displacements of the resonator with at least one of a plurality of amplitudes or frequencies.

In another aspect combinable with any one of the previous aspects, actuating the resonator with an actuation protocol includes inducing a measurable change on a motion of the resonator based at least in part due to one or more deformations in the fluid sample.

In another aspect combinable with any one of the previous aspects, measuring at least one characteristic of the resonator includes measuring at least one characteristic in a transduction domain that provides a measurable signal from the operation of the resonator.

In another aspect combinable with any one of the previous aspects, measuring at least one characteristic in a transduction domain that includes at least one of a capacitive, a piezoelectric, a magnetic, or an optical characteristic.

In another aspect combinable with any one of the previous aspects, measuring at least one characteristic of the resonator includes measuring at least one of a velocity or a displacement of amplitude or phase of the resonator in at least one of a time domain or a frequency domain.

In another aspect combinable with any one of the previous aspects, comparing the at least one measured characteristic to a rheological model includes comparing at least one motion characteristic of the resonator to at least one of a mathematical model or a computational model.

In another aspect combinable with any one of the previous aspects, the at least one of the mathematical model or the computational model relates a change in the at least one motion characteristic to at least one of a deformation amplitude or a deformation rate induced in the fluid sample.

In another aspect combinable with any one of the previous aspects, actuating the resonator disposed in the volume that contains the fluid sample to operate the resonator in the fluid sample at the predetermined actuation scheme includes actuating a mechanical resonator disposed in the volume that contains the fluid sample to vibrate the mechanical resonator in the fluid sample at a predetermined vibration protocol.

In another aspect combinable with any one of the previous aspects, measuring the at least one characteristic of the resonator based on the operation of the resonator in the fluid sample includes measuring at least one motion characteristic of the mechanical resonator based on a non-linear response of the mechanical resonator in the fluid sample.

In another aspect combinable with any one of the previous aspects, comparing the at least one measured characteristic to a rheological model that associates characteristics of the fluid sample to one or more rheological properties includes comparing the at least one measured motion characteristic to the rheological model that associates motion characteristics of the fluid sample to one or more rheological properties.

In another aspect combinable with any one of the previous aspects, measuring the at least one motion characteristic of the mechanical resonator includes measuring the at least one motion characteristic with a photodetector positioned to receive a reflected laser beam that originates with a laser beam source and reflects from the vibrating mechanical resonator.

Another aspect combinable with any one of the previous aspects further includes circulating the fluid sample into the volume during actuation of the resonator.

In another aspect combinable with any one of the previous aspects, determining one or more rheological properties of the fluid sample includes iteratively determining the one or more rheological properties of the fluid sample with a numerical inversion or optimization protocol.

In another aspect combinable with any one of the previous aspects, the one or more rheological properties includes at least one of a complex viscosity, a storage modulus, a loss modulus, an apparent viscosity, a flow index, or a consistency factor of the fluid sample.

In another aspect combinable with any one of the previous aspects, the rheological model includes at least one of a Bingham Plastic model, a power law model, a Hershel-Bulkley model, or a Carreau model.

In another aspect combinable with any one of the previous aspects, the fluid sample includes a non-Newtonian liquid.

In another aspect combinable with any one of the previous aspects, the non-Newtonian liquid includes a hydrocarbon liquid, a completion liquid, or a petroleum-derived liquid.

Another general implementation includes a rheological property measurement system that includes a container that includes a volume that encloses a fluid sample; a resonator disposed within the volume and in contact with the fluid sample; a detector positioned to measure at least one characteristic of the resonator based on an operation of the resonator in the fluid sample; and a control system communicably coupled to at least the resonator and the detector. The control system is configured to perform operations including actuating a resonator disposed in a volume that contains a fluid sample to operate the resonator in the fluid sample at a predetermined actuation scheme; measuring at least one characteristic of the resonator based on the operation of the resonator in the fluid sample; comparing the at least one measured characteristic to a rheological model that associates characteristics of the fluid sample to one or more rheological properties; and based on the comparison, determining one or more rheological properties of the fluid sample.

In an aspect combinable with the general implementation, the resonator includes a mechanical resonator.

In another aspect combinable with any one of the previous aspects, the mechanical resonator includes a piezoelectric crystal, a MEMS device, or a tuning fork.

In another aspect combinable with any one of the previous aspects, the operation of actuating the resonator includes actuating motion on the resonator through one or more signals to induce harmonic or anharmonic motion.

In another aspect combinable with any one of the previous aspects, the one or more signals includes one or more capacitive, piezoelectric, magnetic, or optical signals.

In another aspect combinable with any one of the previous aspects, the control system is configured to perform operations further including actuating the resonator with an actuation protocol that actuates the resonator in at least one of a steady state motion or a time-dependent motion.

In another aspect combinable with any one of the previous aspects, the time-dependent motion includes at least one sequence of displacements of the resonator with at least one of a plurality of amplitudes or frequencies.

In another aspect combinable with any one of the previous aspects, the operation of actuating the resonator with an actuation protocol includes inducing a measurable change on a motion of the resonator based at least in part due to one or more deformations in the fluid sample.

In another aspect combinable with any one of the previous aspects, the operation of measuring at least one characteristic of the resonator includes measuring at least one characteristic in a transduction domain that provides a measurable signal from the operation of the resonator.

In another aspect combinable with any one of the previous aspects, the operation of measuring at least one characteristic in a transduction domain that includes at least one of a capacitive, a piezoelectric, a magnetic, or an optical characteristic.

In another aspect combinable with any one of the previous aspects, the operation of measuring at least one characteristic of the resonator includes measuring at least one of a velocity or a displacement of amplitude or phase of the resonator in at least one of a time domain or a frequency domain.

In another aspect combinable with any one of the previous aspects, the operation of comparing the at least one measured characteristic to a rheological model includes comparing at least one motion characteristic of the resonator to at least one of a mathematical model or a computational model.

In another aspect combinable with any one of the previous aspects, the at least one of the mathematical model or the computational model relates a change in the at least one motion characteristic to at least one of a deformation amplitude or a deformation rate induced in the fluid sample.

In another aspect combinable with any one of the previous aspects, the operation of actuating the resonator disposed in the volume that contains the fluid sample to operate the resonator in the fluid sample at the predetermined actuation scheme includes actuating a mechanical resonator disposed in the volume that contains the fluid sample to vibrate the mechanical resonator in the fluid sample at a predetermined vibration protocol.

In another aspect combinable with any one of the previous aspects, the operation of measuring the at least one characteristic of the resonator based on the operation of the resonator in the fluid sample includes measuring at least one motion characteristic of the mechanical resonator based on a non-linear response of the mechanical resonator in the fluid sample.

In another aspect combinable with any one of the previous aspects, the operation of comparing the at least one measured characteristic to a rheological model that associates characteristics of the fluid sample to one or more rheological properties includes comparing the at least one measured motion characteristic to the rheological model that associates motion characteristics of the fluid sample to one or more rheological properties.

In another aspect combinable with any one of the previous aspects, the operation of measuring the at least one motion characteristic of the mechanical resonator includes measuring the at least one motion characteristic with a photodetector positioned to receive a reflected laser beam that originates with a laser beam source and reflects from the vibrating mechanical resonator.

In another aspect combinable with any one of the previous aspects, the control system is configured to perform operations further including controlling a pump to circulate the fluid sample into the volume during actuation of the resonator.

In another aspect combinable with any one of the previous aspects, the operation of determining one or more rheological properties of the fluid sample includes iteratively determining the one or more rheological properties of the fluid sample with a numerical inversion or optimization protocol.

In another aspect combinable with any one of the previous aspects, the one or more rheological properties includes at least one of a complex viscosity, a storage modulus, a loss modulus, an apparent viscosity, a flow index, or a consistency factor of the fluid sample.

In another aspect combinable with any one of the previous aspects, the rheological model includes at least one of a Bingham Plastic model, a power law model, a Hershel-Bulkley model, or a Carreau model.

In another aspect combinable with any one of the previous aspects, the fluid sample includes a non-Newtonian liquid.

In another aspect combinable with any one of the previous aspects, the non-Newtonian liquid includes a hydrocarbon liquid, a completion liquid, or a petroleum-derived liquid.

Implementations according to the present disclosure may include one or more of the following features. For example, implementations according to the present disclosure may determine rheological properties of a fluid sample with minimally invasive and localized measurements, unlike conventional techniques which are either based on fixed fluid deformation rates that give no information about rheology or require cumbersome probes such as rotational rods driven by torque calibrated motors. As another example, implementations according to the present disclosure may determine rheological properties of complex fluids, such as refining process fluids, drilling fluids, and other hydrocarbon fluids, in which non-linear rheological measurements as described in this disclosure provide more rich information about structural changes in the fluid than steady rotational, capillary and other conventional rheological measurements. As another example, implementations according to the present disclosure may determine rheological properties by exploiting non-linear damping characteristics rather than focusing only on calculating a complex viscosity from the hydrodynamic force equation to obtain the viscoelastic properties of the fluid from the storage and viscous modulus.

The details of one or more implementations of the subject matter described in this disclosure are set forth in the accompanying drawings and the description. Other features, aspects, and advantages of the subject matter will become apparent from the description, the drawings, and the claims.

DETAILED DESCRIPTION

In example implementations, a rheological property measurement system may make inline measurement of rheological properties of fluids (for example, non-Newtonian fluids), which properties are often important to monitor during processes and to check for purposes of quality control. For example, the rheological property measurement system may determine properties of fluids used in the upstream oil industry such as fluids for drilling, hydraulic fracturing, and production stimulation of subterranean wells. Example implementations of the rheological property measurement system may also determine properties of fluids used in a downstream or chemicals industry, such as petroleum-derived products in refining and chemical production. Because contamination, damage to fluids, or changes in the quality of products can manifest as a change in the rheological properties of these fluids during their handling, example implementations of the rheological property measurement system may eliminate or help eliminate such changes through the implementation of an inline and real-time measurement system.

Example fluids that may be measured by the rheological property measurement system include drilling mud, hydraulic fracturing fluids, and polymers injected into reservoirs for enhanced oil recovery, for example, during usage of such fluids in an upstream recovery process. Many of these fluids are considered non-Newtonian and, thus, their properties may be carefully designed for optimal performance. However, during operations, contamination or damage to the fluids may occur such that they no longer have the intended properties.

The functionality of drilling muds and other wellbore fluids such as fracturing fluids and enhanced recovery polymer fluids is introduced through design of the non-Newtonian characteristics of the fluid. The viscosity dependence on shear and the solid-like properties of the fluid are used, for instance, to keep drill cuttings suspended while the fluid is static during a drilling operation. To maintain the desired properties of the fluid, it may be preferable to have constant inspection of the viscosity and density of the fluid (at the very least). However, due to the non-Newtonian properties of these fluids (shear dependent viscosity) full rheological characterization of such fluids is also desirable and may be determined by the example implementations of the rheological property measurement system. Furthermore, real-time measurement of these properties with the rheological property measurement system described in the present disclosure may allow better optimization and automation of the operations that use these fluids (for example, drilling, production).

Figure 1:
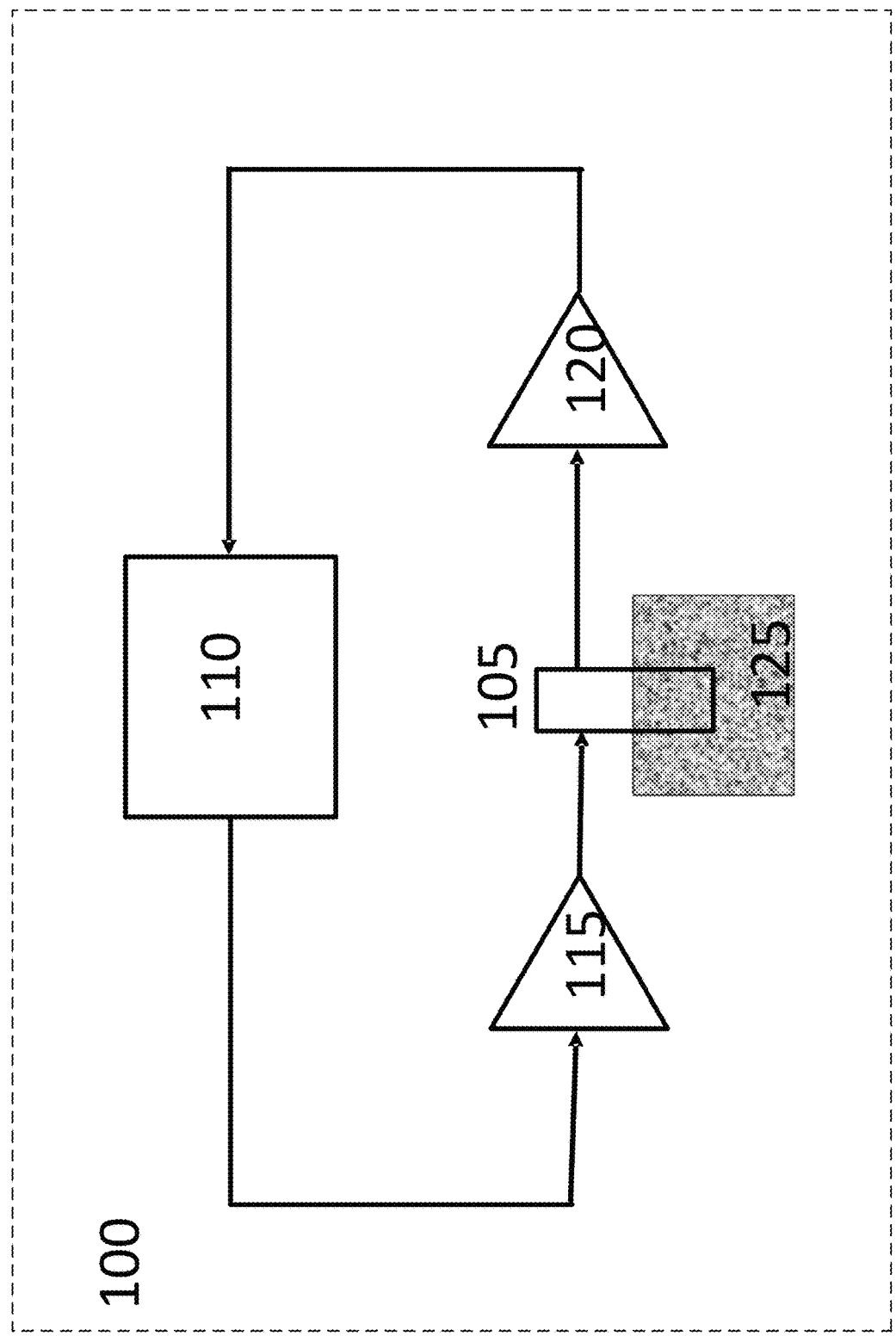
FIG. 1 is a block diagram of an example implementation of a rheological property measurement system according to the present disclosure

FIG. 1 is a block diagram of an example implementation of a rheological property measurement system 100. As illustrated, the system 100 includes a fluid sample 125 and a resonator 105 (for example, a mechanical resonator, also called a "sensor" in some aspects). In this example, the resonator is in contact with the fluid sample 125, which may be, for example, a non-Newtonian fluid. For example, in some aspects, the resonator 105 is immersed in the fluid sample 125 (for example, within a pipeline, container, or other enclosure).

System 100 also includes an actuator 115 that is communicably coupled to the resonator 105. The actuator 115 may be operated to cause motion of the resonator 105 within the fluid sample 125, for example by applying a force or displacement to the resonator. In some aspects, a particular sequence of forces or displacements, called an actuation scheme, may be applied by the actuator 115 acting on the resonator 105 in order to produce motion of the resonator within the fluid sample 125.

In the illustrated example of system 100, a detector 120 is also communicably coupled with the resonator 105. The detector 120, for example, is positioned (for example, within or external to the fluid sample 125) to detect dynamics, such as motion, strains, or stresses, of the resonator 105 during operation of the system 100. The motion of the resonator 105 in response to the actuation scheme may be changed or affected by one or more fluid properties of the fluid sample 125, and measured by the detector 120.

System 100 also includes a control system (or controller) 110 that is communicably coupled to the actuator 115. The controller 110, in this example, may provide a human-machine interface for an operator of the system 100 to operate the actuator 115 to initiate a particular actuation scheme of the resonator 105.

In an example operation of system 100, a human-operator may operate the controller 110 to control the actuator 115 to apply a certain sequence of motions or forces to the resonator 105. For example, the controller 110 can control the actuator 115 to apply to the resonator 105 a pre-determined sequence (for example, according to a known or pre-set actuation scheme) or a unique sequence of displacements, strains, forces, or stresses. The resonator 105 can then move within the fluid sample 125 in response to the actuation scheme and influenced by the rheological properties of the fluid sample 125. The dynamics of the resonator 105 in response to the actuation scheme will be sensed by the detector 120. The detector 120 can sense the dynamics of the resonator, converting these dynamics to a measurable signal output. In some aspects, the measurable output is provided (for example, to the controller 110) which determines one or more fluid properties of the fluid sample 125 based on measured characteristics of the detector output in response to the actuation scheme. For example, the fluid properties can be rheological properties, such as a complex viscosity, a storage modulus, a loss modulus, an apparent viscosity, a flow index, or a consistency factor.

As described, the actuator 115 can initiate operation of the resonator 105 with a particular, pre-determined actuation scheme. Some example schemes include a sinusoidal excitation, other periodic excitation waveforms, a non-periodic excitation such as a pulse, impulse, or step excitation, the parametric sweep technique, a multi-parametric actuation/detection technique, or the ring-up/ring-down technique, where measurement of the decay envelope of the vibrations is performed while the actuation is switched on and off. The parametric study, for example, can operate the actuator 115 such that a particular factor is varied through a range of values during the operation, while all other factors of the operation are held fixed at a baseline value. Each factor can be varied through a range, in turn, while the other operational factors may be held at a baseline. For example, the actuation force may be varied through a range of values so that a range of different oscillation amplitudes deform the fluid at different shear-rates, thus allowing the construction of a rheogram from the measured changes in the damping force (for example, viscosity) as a function of imposed shear-rates.

In some aspects, a non-Newtonian fluid can produce a non-linear relationship between the detector signal and the actuator signal such that measurable characteristics of the detector signal produced by the non-linear relationship to the actuator signal can be related to rheological parameters of the non-Newtonian fluid. For example, in a Newtonian fluid, the detected amplitude of stress or motion of the resonator would be proportional to the motion or stress applied to the resonator by the actuator. In a non-Newtonian fluid, however, this proportionality may not apply. For example, if a certain actuator motion produced a certain detected force on the resonator, an actuator motion which is twice as large would produce a detected force which is twice as large in a Newtonian fluid, less than twice as large in a non-Newtonian shear-thinning fluid, and more than twice as large in a non-Newtonian shear-thickening fluid. Similarly, if a certain actuator force produces a detected resonator motion, then an actuator force twice as large would produce twice the motion in a Newtonian fluid, more than twice the motion in a shear-thinning fluid, and less than twice the motion in a shear thickening fluid.

Accordingly, parameters of the shear-thinning or shear-thickening rheological behavior of a non-Newtonian fluid can be obtained by an actuation scheme where sinusoidal signals of two or more different amplitudes are applied in sequence to control the actuator and the amplitude of the detected signal is measured for each actuation amplitude. In another actuation scheme, the resonator is actuated with a sinusoidal signal of varying amplitude and the corresponding amplitude of the detected signal is related to the parameters of a model for a non-Newtonian fluid. All such activation schemes and measured properties of the detected signal are within the scope of this disclosure.

In some aspects, the non-linear response of a resonator in a non-Newtonian fluid is such that the resonator can produce harmonics of the actuation frequency. For example, if the resonator is actuated at a given frequency, the detected motion will contain energy at the actuation frequency as well as energy at harmonics or multiples of the actuation frequency, for example at twice the actuation frequency. Accordingly, the parameters of a model describing the non-Newtonian shear stress versus strain rate characteristic of a fluid can be determined by measuring in the detected signal, for example, the amplitudes and phases of the fundamental and harmonics of the actuation frequency. All such actuation schemes and measured properties of the detected signal are within the scope of this disclosure.

In some aspects, if two frequencies are present in the actuation signal, the non-linear dynamics of the resonator in a non-Newtonian fluid can produce sum and difference frequencies in the response of the resonator and that the amplitudes and phases of the sum frequency or difference frequency can be related to parameters of a model describing the non-Newtonian rheology of the fluid. All such actuation schemes and measured properties of the detected signal are within the scope of this disclosure.

In example implementations, the relative phase between the drive signal controlling the actuator 115 and the measured signal from the detector 120 is monitored as the amplitude of the drive signal is varied. Through a spectral analyzer system, for example, the in-phase and out-of-phase components of the signal from the detector relative to the signal controlling the actuator can then be obtained and used to determine rheological properties such as the storage and viscous moduli. The frequency of the actuation signal (for example, signal controlling the actuator) may also be varied parametrically around a bandwidth of interest, where a resonant peak for any given vibrational mode may exist. The amplitude and phase of the output signal may then be obtained with or by a spectral analyzer system, as mentioned previously, and the transfer function of the system may then be obtained and fitted to the appropriate mathematical model including the shear-dependent damping (for example, viscosity). For example, depending on the geometry of the resonator 105, a spatial distribution of shear-rates may be induced around the vibrating body of the resonator as the fluid is displaced and deformed. Through mathematical or computational modeling, the measured transfer function including a damping force model related to a specific rheological model can be used to extract the rheological parameters of the fluid. Alternatively, a multi-parametric study can also be performed, where a complex input signal containing a plurality of components with different frequencies, amplitudes, and phases may be used to drive the resonator. For example, by using two sinusoidal signals near one of the resonant modes of the detector 120, a characteristic harmonic distortion in the oscillatory output signal may be obtained due to nonlinear changes in the viscous dissipative forces from the fluid. The resonator 105 can then be operated at a particular range or variety of frequencies and measuring the induced harmonic distortion within a certain bandwidth. The obtained spectra may then be related to the rheological profile of the device by appropriate mathematical or computational modeling.

The decay envelope measurement technique can be used when the resonator 105 is actuated to oscillate at a determined amplitude and, after a stable oscillation is established, the drive signal is removed allowing the amplitude of oscillation to decay. Deviations from a pure exponential decay in the decay envelope can then be used to obtain parameters of a model describing a non-Newtonian fluid. Relating the measured characteristics of the detected motion of the resonator to parameters of a rheological model for the non-Newtonian fluid can be accomplished by applying the selected actuation scheme, collecting measured characteristics of the detected resonator motion for non-Newtonian test fluids for which the parameters of a rheological model are known, and using, for example, non-linear statistical regression to establish an equation relating the parameters to the measured characteristics. Alternatively, the measured characteristics and associated model parameters can be organized as a lookup table, where interpolation (for example, linear interpolation, or spline interpolation) are used to find interpolated model parameters based on how close the measured characteristics for an unknown sample are to the measured characteristics for one or more test fluids.

The actuator is, in some examples, a transducer that converts an electrical signal into a mechanical property at the resonator, such as a displacement, a velocity, an acceleration, a strain, a stress, or a force, proportional in magnitude to the electrical signal. Such transducers include, but are not limited to: a piezoelectric crystal, a solenoid, a magneto-strictive material, a linear motor comprising a coil that produces a magnetic field and a permanent magnet that experiences a force in response to the field, and a capacitive actuator where an electric field produces a force between charged electrodes. The detector is preferentially a transducer that converts a mechanical property at the resonator, such as a displacement, a velocity, an acceleration, a strain, a stress, or a force to an electrical signal, proportional in magnitude to the mechanical property Such transducers include, but are not limited to: a piezoelectric element, a capacitive sensor, an inductor with a core attached to the resonator, a piezoresistive element, a strain sensor, a force sensor, a pressure sensor, a linear variable differential transformer, a linear variable inductance sensor, a magnetostrictive element, and a photodetector.

Figure 2:
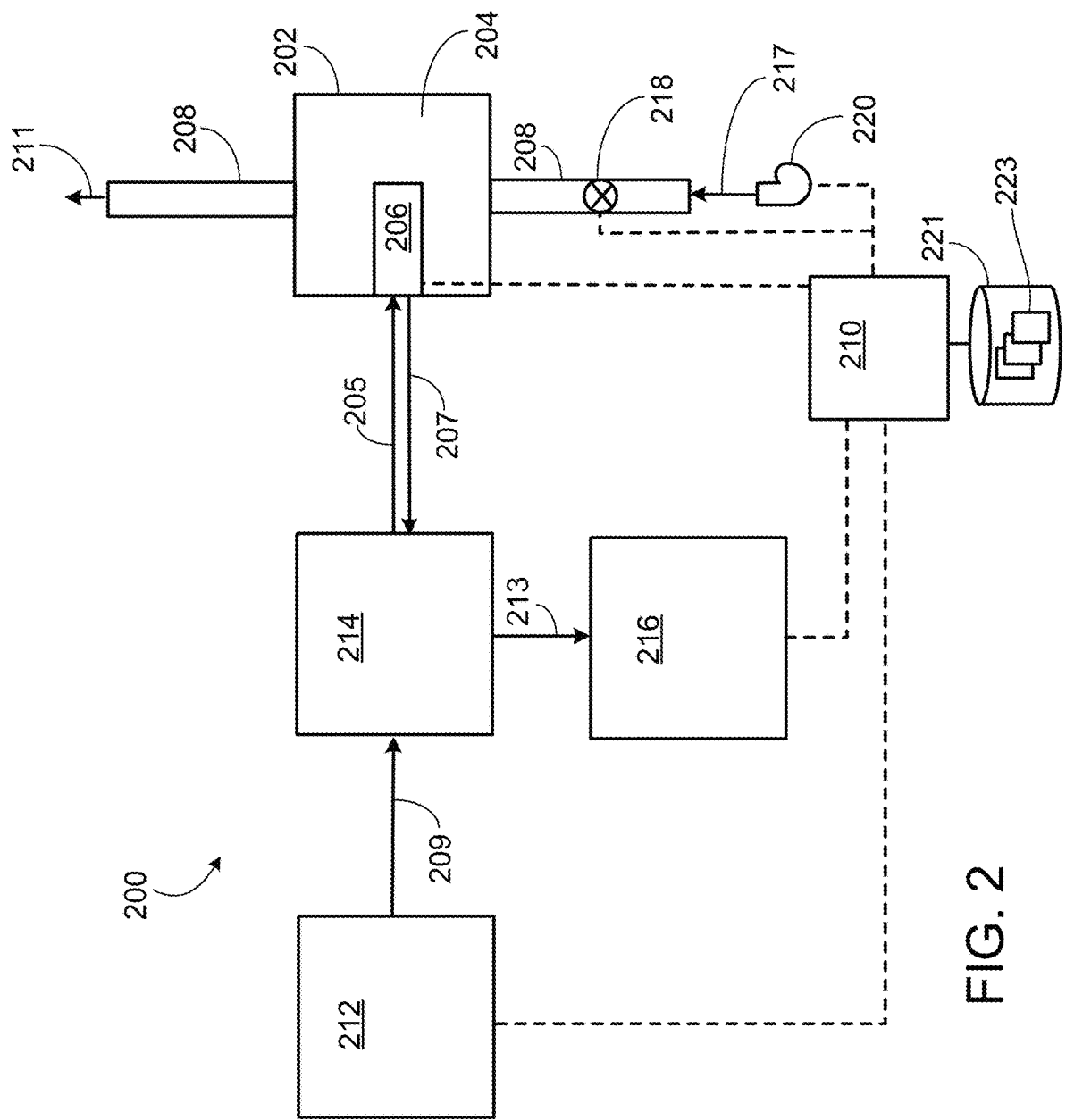
FIG. 2 is a schematic illustration of an example implementation of a rheological property measurement system according to the present disclosure.
Figure 3:
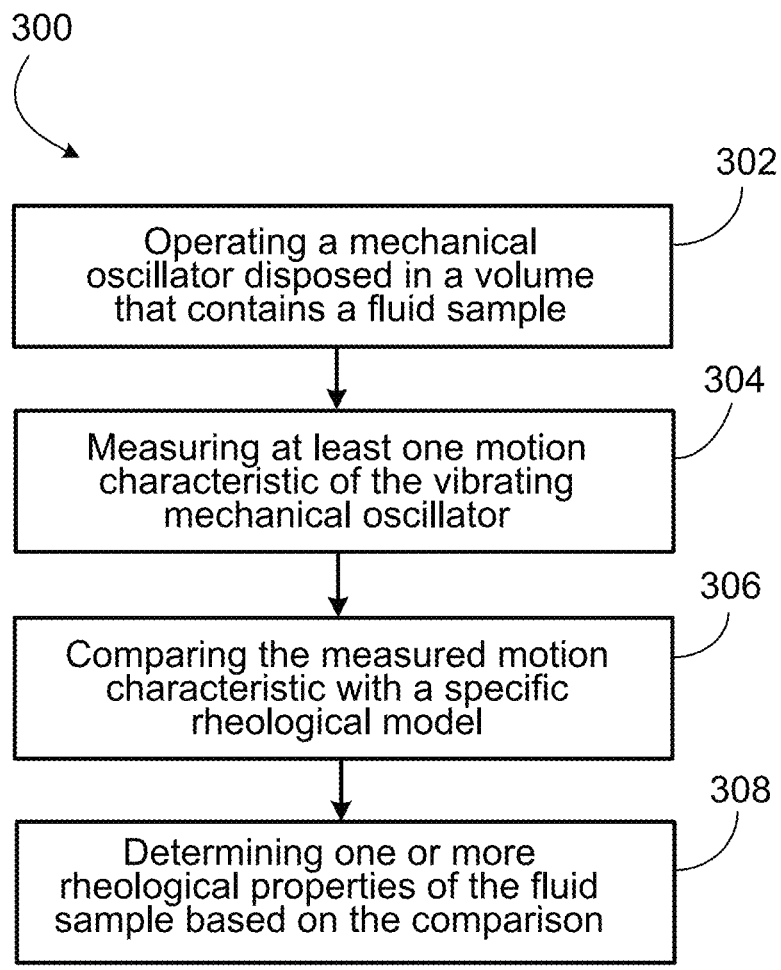
FIG. 3 is flowchart that describes an example implementation of a method for determining rheological properties of a fluid sample according to the present disclosure.

FIG. 3 is flowchart that describes an example implementation of a method 300 for determining rheological properties of a fluid sample. Method 300, for example, may describe an example operation of or with the rheological property measurement system 200 shown in FIG. 2. For example, one or more steps of method 300 may be executed by or with the control system 210 of the rheological property measurement system 200.

Method 300 may begin at step 302, which includes operating a mechanical resonator disposed in a volume that contains a fluid sample. For example, the control system 210 may actuate the mechanical resonator 206 (for example, a resonator, or mechanical resonator, such as a piezoelectric crystal, a MEMS device, or any vibrating device) while the resonator 206 is disposed in the volume of fluid sample 204. The control system 210 may actuate the resonator 206 by, for example, capacitive, piezoelectric, magnetic, optical or any other physical signal or combination of signals to induce harmonic or anharmonic motion of the resonator 206 in the fluid sample 204.

The resonator is comprised of a mechanical structure which supports vibrations and may include intrinsically or extrinsically the actuator and/or detector of said vibrations. It may be fabricated by traditional subtractive machining processes through milling, drilling, turning, or other machine-aided processes, manual or automatic. It may be comprised of any material able to support vibrations on the machined mechanical structure such as metals, silicon, silicon-nitride, quartz lithium niobite, silicon carbide, or any other crystal, natural material, or alloy compatible with said machining processes. The mechanical structure may be fabricated into any shape such as cantilevers, beams, wires, plates, tuning forks, or any other geometry able to produce flexural, torsional or bulk mechanical vibrations. Other fabrication methods may be additive, which can also include "additive manufacturing," or 3D-printing. These may be used to fabricate the mechanical structure or to add function or features to the mechanical structure such as, but not limited to, actuation capabilities, or detection capabilities. Furthermore, these functions or features may be added via commercially available components such as strain gauges, piezoelectric elements, magnets, external coils, pressure or acoustic sensors, accelerometers, lasers, or photodetectors. The fabrication process may include, in part or in total, micro or nanomachining steps such as optical lithography, electron beam lithography, soft lithography, film deposition, physical or chemical evaporation techniques, etching processes, bonding, or other bottom-up or top-down micro/nano assembly or patterning techniques. These may be used to fabricate any or the total of the components including the mechanical structure, actuators, or detectors. The mechanical structure, actuators, and/or detectors may be of sizes spanning the nanometer scale to macroscopic sizes. The mechanical structure size and stiffness may therefore span a large band of vibrational modes with frequencies from Hertz to tens or hundreds of megahertz for flexural and torsional resonators, and up to gigahertz frequencies for bulk-mode resonators.

Step 302 may also include establishing or implementing (or both) an actuation protocol of the mechanical resonator 206 in which the resonator 206 is set either in steady-state motion or is controlled to vibrate through a time sequence of displacements at various amplitudes or frequencies that would induce a predictable (theoretically or computationally) spatial distribution of deformations (or deformation history) on the fluid sample 204 at any given time. Thus, there may be a measurable change of the motion of the mechanical resonator 206 induced and, thereby, inducing a measurable change on the motion of the device due to the changes in the properties of the fluid from said deformations.

The motion of the resonator may be periodic or non-periodic. Periodic motion may include harmonic and anharmonic motion of single or multiple frequency components as well as quasi-periodic motion at incommensurable frequencies. Non-periodic motion may include at least one component of the motion that cannot be represented by a periodic function, such as the exponential envelope of an exponentially decaying or growing oscillatory signal.

The frequency or frequencies of motion of the resonator may be chosen or designed (via stiffness or size) according to the viscoelastic characteristics of the fluid whereby the response measured by the resonator may be more affected by either viscous or elastic components of the fluid above or below a characteristic fluid relaxation time, or relaxation time spectra, as determined by the fluid's specific microstructural characteristics.

In some aspects, mechanical properties of the particular mechanical resonator 206 can be described (for instance, in the Butterworth-Van Dyke model) as a resonant inductive-capacitive-resistive (LCR) circuit. At resonance, the capacitive (C) and inductive (L) parts of the circuit may cancel out, leaving only a resistive (R) component. Thus, a measured current amplitude (I) and the driving voltage (V), corresponding to the velocity and the driving force in the mechanical domain, scale linearly according to:

$$I = \left(\frac{1}{R}\right)V,$$

when the resistance (equivalent to the damping in the mechanical domain) is constant. Changes in the damping as a function of excitation amplitude indicate changes in the viscosity of the fluid, since the damping coefficient is dependent on geometrical parameters of the mechanical resonator 206 and the viscosity of the fluid sample 204.

Figure 4:
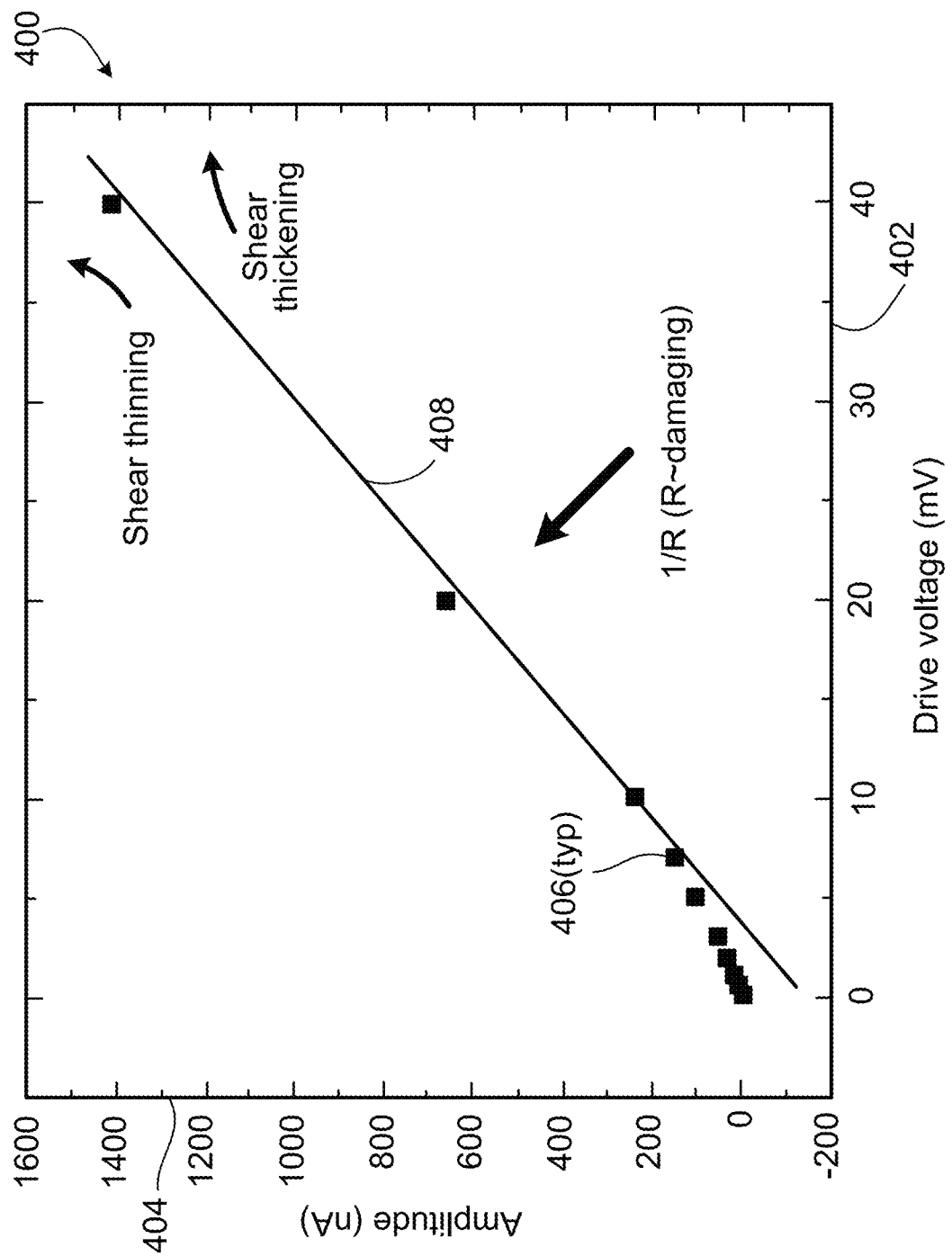
FIG. 4 is a graph that illustrates an example of linear dependence of measured current as a function of excitation amplitude in a mechanical resonator that is used in the method of FIG. 3.

Turning briefly to FIG. 4, this figure shows a graph 400 that illustrates an example of linear dependence of measured current as a function of excitation amplitude in a mechanical resonator that is used in the process of FIG. 3. Graph 400 includes an x-axis 402 that shows drive voltage in millivolt (mV) and a y-axis 404 that shows amplitude in nanoamperes (nA). Plotted points 406 represent measured current versus excitation voltage for the mechanical resonator 206 (for example, a piezoelectric tuning fork device) in vacuum. Graph 400 also includes a fitted curve 408 according to the plotted points 406 that separate a shear thinning region and a shear thickening region, as shown.

In graph 400, the resistive component (R) represents the dominant constant damping from the intrinsic mechanical properties of the resonator 206 since it is in vacuum. When the mechanical resonator 206 is immersed in the fluid sample 204, $$R = R_i + R_{fluid},$$

where $R_i$ and $R_{fluid}$ represent the intrinsic and the fluid damping, respectively. When the fluid environment is a liquid (such as fluid sample 204), the $R_{fluid}$ dominates the damping and $R_i$ can be ignored. In this case, at large excitations, deviations from linear dependence would indicate either shear thinning or shear thickening, as illustrated in graph 400. The rate of deviation of the damping could then be represented as a power law of the such that $$R(v) \sim \mu(v) \sim v^{\alpha},$$

where $\mu(v)$ represents viscosity, v is the velocity of oscillation, and $\alpha$ is a constant coefficient. The damping force, $F_D$, on the mechanical resonator 206 can then be expressed as:

$$F_D = c_0 \mu(v) v = c_0 \mu_0 v^{1+\alpha},$$

where $c_0$ and $\mu_0$ represent the geometrical and viscous factors in the linear regime. By analytical or computational means, the fluid structure interaction (stress and fluid velocity distribution around the moving resonator 206), depending on the geometry of the resonator 206, would allow the conversion of damping force versus velocity to shear stress ($\sigma(\dot{\gamma})$) versus shear rate ($\dot{\gamma}$) such that a constitutive equation can be written and a rheological model (for example, to use in step 306) can be constructed.

Method 300 may continue at step 304, which includes measuring at least one motion characteristic of the vibrating mechanical resonator. For example, the control system 210 may operate the laser beam source 212 to generate a laser beam (for example, a HeNe laser beam) that passes over the beam splitter 214 to reflect a portion to the photodetector 216 and a portion toward the mechanical resonator 206. In some aspects, a motion characteristic of the vibrating resonator 206 may be measured via capacitive, piezoelectric, magnetic, optical or any other transduction domain that provides a measurable signal from the motion of the mechanical resonator 206. In some aspects, the motion characteristic may be one or more of a velocity or displacement amplitude of the resonator 206, a phase of the resonator 206, or any characteristic of the motion, or (linear or nonlinear) combination of motions, of the mechanical resonator 206, in time or frequency domain, as induced by the actuation protocol of the resonator 206 by the control system 210.

Method 300 may continue at step 306, which includes comparing the measured motion characteristic with a specified rheological model. For example, the rheological model may be a mathematical or a computational model that predicts a change in one or more motion characteristics of the fluid sample 204 according to a deformation amplitude (or amplitudes) and a deformation rate (or rates) induced in the fluid sample 204. The chosen rheological model may also account for, for example, the known geometry of the mechanical resonator 206, and the imposed actuation protocol.

In some aspects, when the mechanical resonator 206 is actuated by electrical or magnetic means and vibrated in a Newtonian fluid, it will experience a damping force that is proportional to the instantaneous velocity of the resonator 206. When the mechanical resonator 206 is vibrated in a non-Newtonian fluid (such as, in some aspects, fluid sample 204), this damping force is related to the velocity of the resonator 206 in a non-linear way. For example, in non-Newtonian fluids, the damping force may increase or decrease relative to the linear trend. A fluid where the damping force grows above the linear trend at large velocity is called a "shear-thickening" fluid and if the damping force decrease below the linear trend at large velocity the fluid is called "shear-thinning." Rheological models, such as the Hershel-Bulkley model, may describe this non-linear dependence of damping force on velocity in non-Newtonian fluids. The Hershel-Bulkley model is:

$$\sigma = \sigma_0 + k\dot{\gamma}^n,$$

where $\sigma$ is the shear stress, $\sigma_0$ is the yield stress, $\dot{\gamma}$ is the shear rate, k is the consistency index, and n is the flow index. Fluids described by this relation are yield-stress fluids. When an object moves in a yield-stress fluid, a minimal force which depends on the cross sectional area of the resonator 106 and the yield stress ($\sigma_0$) is applied to start the motion:

$$F_D = \alpha L^2 \sigma_0,$$

where L is the characteristic size of the resonator 206 and $\alpha$ is a constant that indicates that the relevant deformation for yielding extends beyond the surface of the resonator 206. When the resonator 206 is set in motion, an additional velocity dependent component to the damping force is added such that:

$$F_D = \alpha L^2 \left[\sigma_0 + k\left(\frac{v}{l}\right)^n\right],$$

where l represents a length-scale which defines the fluidized region bounded by the un-yielded region in the fluid sample 204.

Method 300 may continue at step 308, which includes determining one or more rheological properties of the fluid sample based on the comparison. For example, in some aspects, the rheological properties of one or more of complex viscosity, storage modulus (G'), loss modulus (G"), as well as steady state shear properties such as apparent viscosity, flow index, and consistency factor may be determined in step 308. In some aspects, the comparison includes iteratively determining, via nonlinear fitting, inversion, or optimization, the rheological parameters of the chosen rheological model that best describe the measured motion characteristics of the motion of the mechanical resonator 206.

In some aspects, step 308 includes an inversion analysis, in which both the solid characteristics of the mechanical resonator 206 and non-Newtonian fluid characteristics of the fluid sample 204 (and their interaction) into account. In such aspects, it may be assumed that the mechanical resonator 206 is fully immersed in the fluid sample 204, and also that motion of the resonator 206 may not be influenced by the presence of boundary or free surface to simplify the inversion analysis. The solid side is driven by a forcing mechanism into a motion and the motion can be modelled as:

$$m\ddot{y} + c_s(\dot{y})\dot{y} + ky = F(t) + R(t),$$

where m is a mass of moving part (the resonator 106), $c_s$ is a structural damping, k is a spring constant, F(t) is the driving force, and R(t) is the reaction force to the mass from surrounding fluid. Assuming that the resonator 106 is moved in a vacuum or thin air, R(t) is negligibly small and can be set to zero. In a highly viscous media, R(t) can make the system underdamped, leading to no oscillation of the resonator 106. R(t) is computed from the stress field in the fluid, more precisely on the solid surface.

The reaction force R(t) is composed of a pressure term and a viscous term. For example, in a Newtonian fluid:

$$R_i(t) = =$$

$$\int \sigma_{ij} n_j dS = \int (-p\delta_{ij} + \tau_{ij}) n_j dS = \int\int \left(-p\delta_{ij} + v\left(\frac{\partial u_i}{\partial x_j} + \frac{\partial u_j}{\partial x_i}\right)\right) n_j dS,$$

where the integration is done over a closed surface, p is pressure, $\delta_{ij}$ is the Kronecker delta, v is viscosity, $\tau_{ij}$ is shear stress, and $n_j$ is the unit vector normal to the surface pointing toward the solid (the resonator 206). The first term explains the reaction force due to the pressure and the second term is due to the friction between the resonator 106 and the fluid sample 204. The fluid side can be described by the Cauchy equation with a non-Newtonian constitutive equation:

$$\frac{\partial \rho}{\partial t} + \nabla \cdot \rho u = 0,$$

$$\rho\left(\frac{\partial u}{\partial t} + u \cdot \nabla u\right) = \nabla \cdot \sigma = -\nabla p + \nabla \cdot \tau,$$

where σ is the stress tensor, and can be related to fluid velocity, u. Non-Newtonian fluid models include Bingham and power-law fluids. For example, the power-law fluid relates τ with velocity, u, using two parameters K and n:

$$\tau_{ij} = K\left(\frac{\partial u_i}{\partial x_j}\right)^n$$

When a rheological model is chosen, then the parameters in the model may be initially unknown. Since these parameters may not be directly observable, they can be estimated using an inversion framework. The inversion framework may include a deterministic approach that minimizes differences between observed measurements and predicted measurements using the selected rheological model and initial parameter values. Specifically, measurements of displacement ($y_o$) or velocity ($\dot{y}_o$) may be taken in step 304 (or at a previous step prior to method 300). Using the selected rheological model, fluid-structure interaction may be simulated, and the simulation gives corresponding modeled quantities, either displacement ($y_m$) or velocity ($\dot{y}_m$), where subscripts, o and m, are the initials of observed and modelled, respectively. The optimization (for example, minimization) problem to solve is:

$$J(p_1,p_2,p_3,\ldots) = \int |y_o - y_m(p_1,p_2,p_3,\ldots)|^2 dt,$$

where ($p_1$, $p_2$, $p_3$, . . . ) are parameters for a rheological model. The example optimization problem is a partial differential equation (PDE)-constrained nonlinear optimization problem that uses regularization terms for stable solution. Computationally, such optimization problems incur many iterations and forward modellings. The optimal solution of the optimization problem is the set of rheological parameters that best explain the measured motion characteristics of the mechanical resonator 206 in the fluid sample 204.

In an example experiment performed with a system such as rheological property measurement system 200, a fluid sample of laponite gel as the fluid sample 204. A piezoelectric crystal tuning fork resonator was used as the mechanical resonator 106, which was actuated by a sinusoidal signal from an external alternating current (AC) signal generator (not shown in FIG. 2). The output of the signal generator was further amplified by a 50X power amplifier in order to generate peak-to-peak voltages above 10 Volts (V). Due to the large excitation voltages and the parasitic capacitance from the piezoelectric crystal, a direct electrical detection of the induced current from the piezoelectric fork's motion was difficult without overloading the detection circuitry. Instead, motion of the resonator was measured optically using the knife edge technique as described with reference to FIG. 2.

A HeNe laser was used as laser beam source 212 and was focused at the edge of a reflective area (metal electrode) on one of the fork's moving prongs, letting half of the laser beam reflect towards a photodetector (216) and the other half transmit through the crystal (resonator 206). This way, as the prong of the fork moved, the intensity of the light was modulated, since the edge of the reflective surface also moves to reflect more or less light during a half period of oscillation. The induced current from the light collected was then a periodic function of the amplitude of oscillation.

This current was then amplified by a current-to-voltage converter and fed into a lock-in amplifier for phase sensitive detection. The reference signal is directly fed from the TTL output of the AC signal generator used to actuate the fork.

In the example experiment, the tuning fork resonator was tested with the above described technique in laponite gel, a model yield-stress fluid similar to typical drilling fluids which is also optically transparent. A mixture of 200 grams of deionized water, 4 grams of laponite and 0.25 grams of sodium hydroxide comprised the fluid sample (204). When immersed in the fluid, a frequency sweep was performed on the tuning fork and resonance peaks were obtained at various excitation voltages as shown in FIG. 5.

Figure 5:
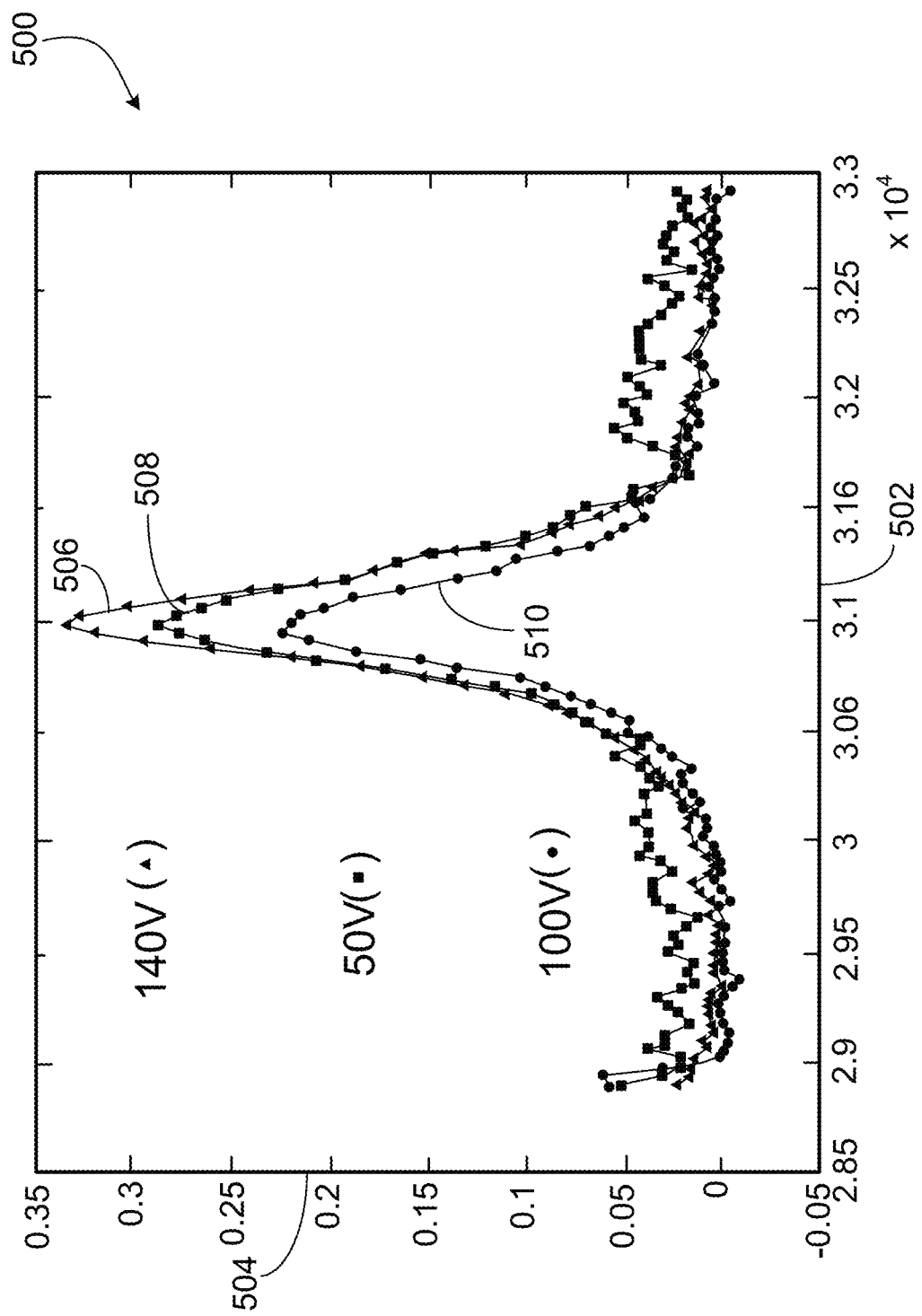
FIG. 5 is a graph that illustrates optically detected resonance peaks for a mechanical resonator immersed in a fluid sample during an experiment according to the method of FIG. 3.

Turning briefly to FIG. 5, this figures shows a graph 500 that illustrates optically detected resonance peaks for a mechanical resonator immersed in a fluid sample during an experiment according to the process of FIG. 3. As shown in FIG. 5, graph 500 includes an x-axis 502 of scanned frequency in Hertz and a y-axis 504 of voltage amplitude in volts. Curves 506, 508, and 510 represent excitation voltages of 140 V, 50 V, and 100 V, respectively.

Figure 6:
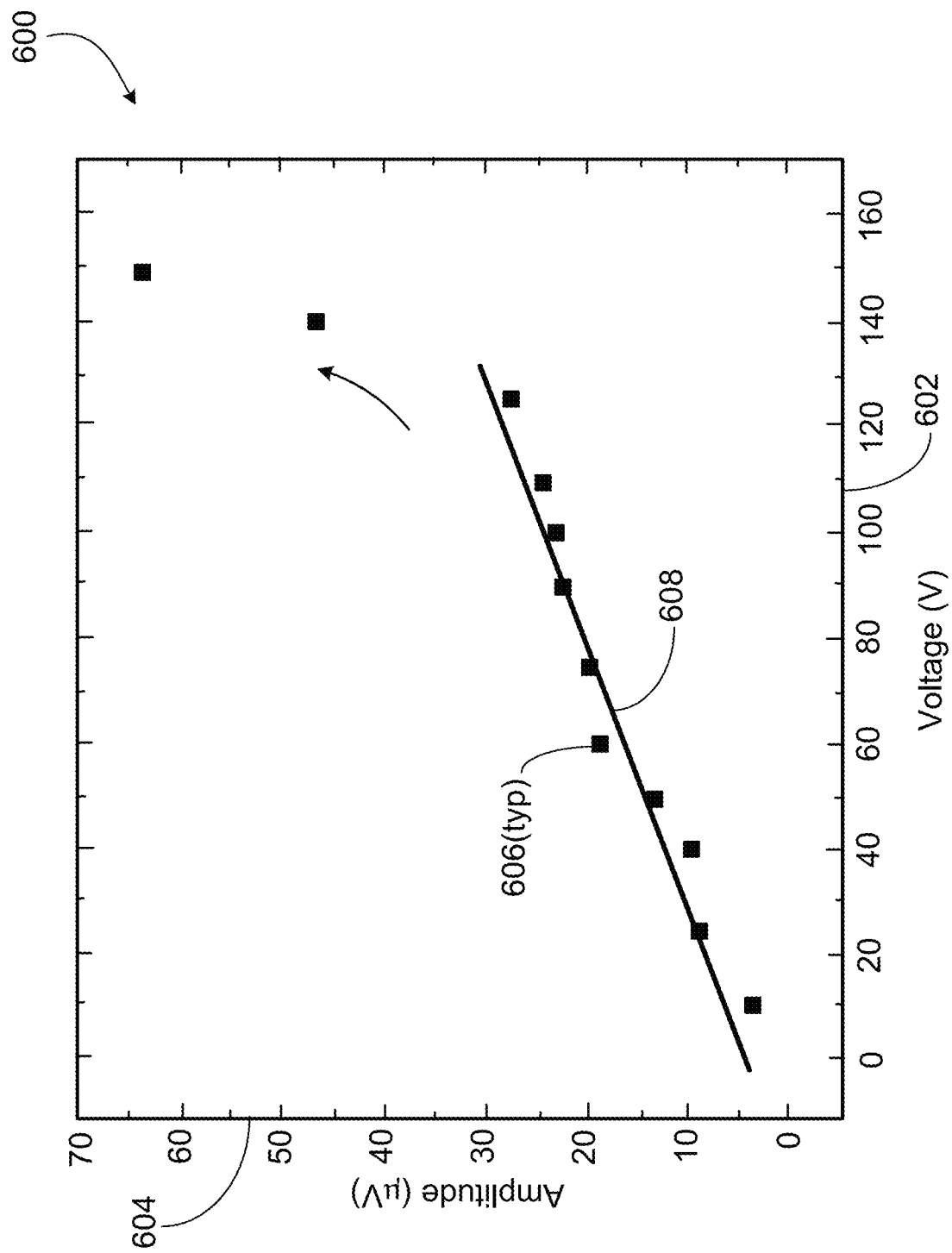
FIG. 6 is a graph that illustrates peak amplitude at resonance for the mechanical resonator immersed in the fluid sample during the experiment according to the method of FIG. 3.

Further, FIG. 6 is a graph 600 that illustrates peak amplitude at resonance for the mechanical resonator immersed in the fluid sample during the experiment according to the process of FIG. 3. Graph 600 includes an x-axis 602 that represents excitation voltage (in volts) and a y-axis 604 that represents peak amplitude at resonance of the tuning fork (in volts). The measured points 606 are shown, as well as a curve 608 fit to a linear portion of the points 606. Here, the peaks were normalized by the excitation voltages. The peak amplitude was extracted by fitting the obtained resonance peak to a model function. As a function of excitation voltage, the amplitude is seen to increase linearly up to 100 V and then begins to deviate (non-linearly).

Figure 7:
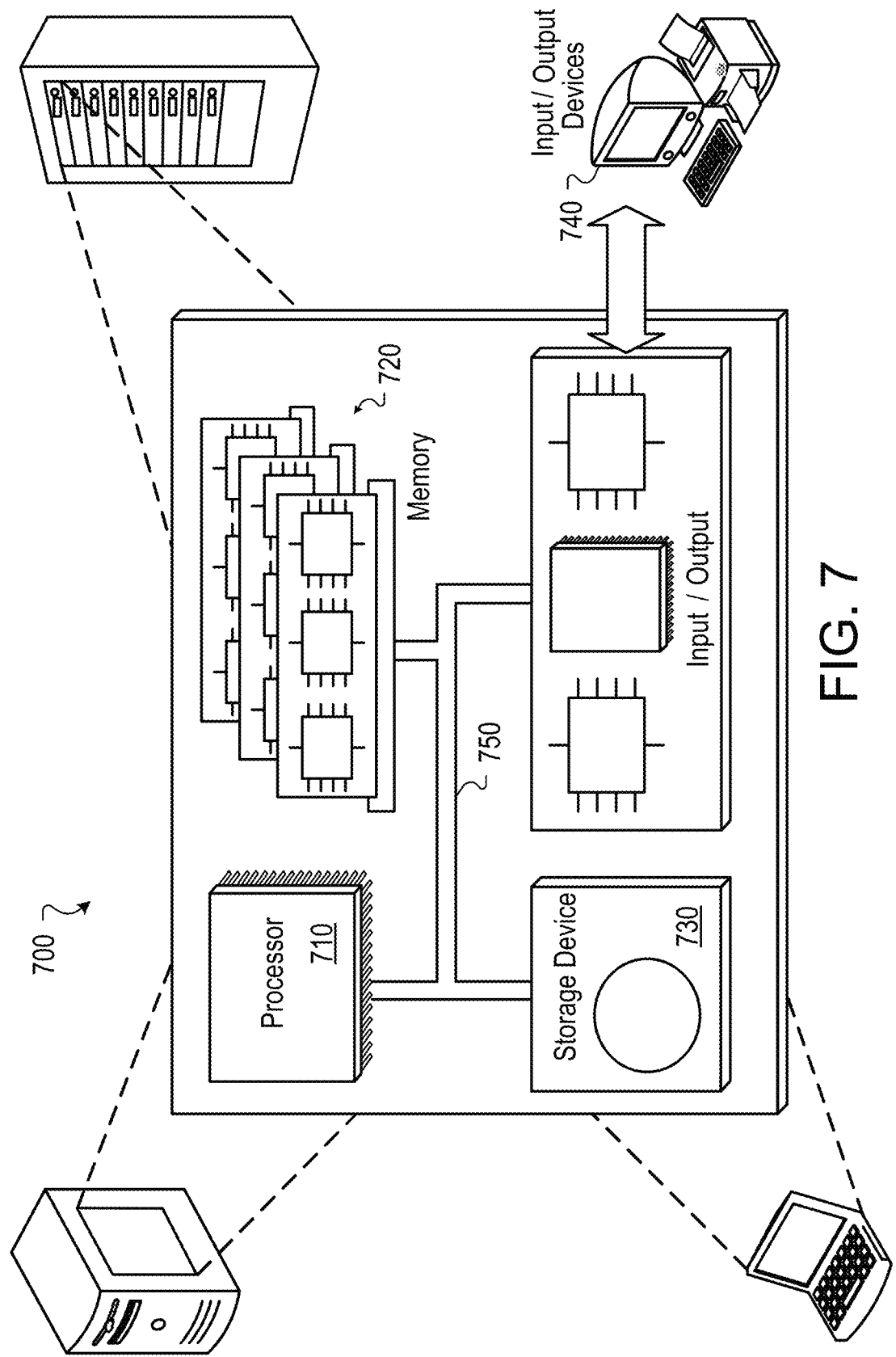
FIG. 7 is a schematic illustration of a controller or control system for a fluid rheology measurement system according to the present disclosure.

FIG. 7 is a schematic illustration of an example controller (or control system) 700 for a rheological property measurement system, such as the control system 210 for rheological property measurement system 200. The controller 700 is intended to include various forms of digital computers, such as printed circuit boards (PCB), processors, or digital circuitry. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 700 includes a processor 710, a memory 720, a storage device 730, and an input/output device 740. Each of the components 710, 720, 730, and 740 are interconnected using a system bus 750. The processor 710 is capable of processing instructions for execution within the controller 700. The processor may be designed using any of a number of architectures. For example, the processor 710 may be a CISC (Complex Instruction Set Computers) processor, a RISC (Reduced Instruction Set Computer) processor, or a MISC (Minimal Instruction Set Computer) processor.

In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the controller 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the controller 700. In one implementation, the storage device 730 is a computer-readable medium. In various different implementations, the storage device 730 may be a floppy disk device, a hard disk device, an optical disk device, a tape device, flash memory, a solid state device (SSD), or a combination thereof.

The input/output device 740 provides input/output operations for the controller 700. In one implementation, the input/output device 740 includes a keyboard or pointing device (or both). In another implementation, the input/output device 740 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as erasable programmable read-only memory (EPROM), electrically erasable programmable read-only memory (EEPROM), solid state drives (SSDs), and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) or LED (light-emitting diode) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described should not be understood as requiring such separation in all implementations, and it should be understood that the described program components and systems can generally be integrated together in a single software product or packaged into multiple software products.

Example Implementations

FIG. 2 is a schematic illustration of a specific implementation of the rheological property measurement system 100. FIG. 2 shows a rheological property measurement system 200 that includes a fluid sample enclosure 202 that can contain or hold a fluid sample 204. Disposed in the enclosure 202 is a mechanical resonator 206 (for example, a resonator) that is in contact with the fluid sample 204. Example implementations of the mechanical resonator 206 include a micro-electro-mechanical system (MEMS) or a piezoelectric flexural resonator (or other piezoelectric vibrating device). Further example include a tuning fork (for example, a piezoelectric crystal tuning fork resonator) that may be actuated by electrical or magnetic energy. In this example, the mechanical resonator 206 is fully immersed in the fluid sample 204.

The rheological property measurement system 200 also includes a laser beam source 212 (for example, an actuator) that is positioned to generate a laser beam 209 toward the mechanical resonator 206. In this example implementation, the laser beam source 212 is a helium-neon (or "HeNe") laser beam source that generates a HeNe laser beam. In this example, the laser beam 209 is directed across a beam splitter 214 that is positioned between the laser beam source 212 and the mechanical resonator 206. Thus, the rheological property measurement system 200 uses the knife-edge technique in which the laser beam 209 is split by the beam splitter 214, and a split portion 213 of the laser beam 209 is reflected toward the photodetector 216, while another split portion 205 of the laser beam 209 is directed toward the mechanical resonator 206. A reflected portion 207 of the split portion 205 of the laser beam 209 reflects back toward the beam splitter 214.

The photodetector 216 (for example, a detector) of the example implementation of the rheological property measurement system 200 is positioned to receive the split portion 213 of the laser beam 209 from the beam splitter 214. Generally, the photodetector 216, through receipt of the split portion 213 of the laser beam 209, measures an intensity of the light from the beam that modulates due to vibration of the mechanical resonator 206. This intensity is converted, by the photodetector 216, into a current magnitude (which may be used as described later to determine one or more motion characteristics of the mechanical resonator 206).

In some implementations, the fluid sample 204 is a static fluid sample. In other words, the fluid sample 204 is not moving (or is insignificantly moving) during operation of the mechanical resonator 206. In an alternative implementation, a flow 217 of the fluid sample 204 may be circulated through conduit 208 and to the fluid sample enclosure 202. In some aspects, a pump 220, a valve 218, or both, may be used to control the flow 217 of the fluid sample 204 into (and out of) the fluid sample enclosure 202. In some aspects, operation of the rheological property measurement system 200 may proceed whether the fluid sample 204 is static or moving, provided that a velocity of the moving fluid sample 204 may need to be such that accurate rheological properties can be determined of the moving sample.

As shown, the example implementation of the rheological property measurement system 200 includes a control system 210 (for example, a controller) that is communicably coupled to at least the mechanical resonator 206, the laser beam source 212, the photodetector 216, the valve 218 and the pump 220. In some aspects, the control system 210 is a stand-alone control system (for example, a hardware computer processor-based control system) that controls such components and may also send data, receive data, or both, to and from such components. Alternatively, control system 210 may represent multiple control systems or controllers, each of which is specifically associated with, for example, the mechanical resonator 206, the laser beam source 212, the photodetector 216, the valve 218 and the pump 220.

As shown, the control system 210 includes or is communicably coupled to a database 221 that stores, for example, one or more predefined rheological models 223. Each of the rheological models 223, in some aspects, is a numerical or computational model that associates rheological properties of a particular fluid (for example, a particular liquid sample) with one or more measured characteristics of the particular fluid. Examples of rheological models include a Bingham Plastic model, a power law model, a Hershel-Bulkley model, or a Carreau model.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method for determining rheological properties of a fluid, comprising:
actuating a resonator disposed in a volume that contains a fluid sample to operate the resonator in the fluid sample at a predetermined actuation scheme;
actuating the resonator with an actuation protocol that actuates the resonator in at least one of a steady state motion or a time-dependent motion, wherein actuating the resonator with an actuation protocol comprises inducing a measurable change on a motion of the resonator based at least in part due to one or more deformations in the fluid sample;
measuring, with a photodetector positioned to receive a reflected laser beam that originates with a laser beam source and reflects from the operating resonator, at least one response characteristic of the resonator based on the operation of the resonator in the fluid sample;
comparing the at least one measured response characteristic to a rheological model that associates the at least one response characteristic of the resonator to one or more rheological properties of the fluid sample; and
based on the comparison, determining one or more rheological properties of the fluid sample.

2. The method of claim 1, wherein the resonator comprises a mechanical oscillator.

3. The method of claim 2, wherein the mechanical oscillator comprises a piezoelectric crystal, a cantilever beam, a MEMS device, a torsional spring, a vibrating wire, or a tuning fork.

4. The method of claim 3, wherein the fluid sample comprises a non-Newtonian liquid.

5. The method of claim 4, wherein the non-Newtonian liquid comprises a hydrocarbon liquid, a completion liquid, or a petroleum-derived liquid.

6. The method of claim 1, wherein actuating the resonator comprises actuating motion on the resonator through one or more signals to induce harmonic or anharmonic motion.

7. The method of claim 6, wherein the one or more signals comprises one or more capacitive, piezoelectric, magnetic, or optical signals.

8. The method of claim 1, wherein the time-dependent motion comprises at least one sequence of displacements of the resonator with at least one of a plurality of amplitudes or frequencies.

9. The method of claim 1, wherein measuring at least one response characteristic of the resonator comprises measuring at least one response characteristic in a transduction domain that provides a measurable signal from the operation of the resonator.

10. The method of claim 9, wherein measuring at least one response characteristic in a transduction domain that comprises at least one of a capacitive, a piezoelectric, a magnetic, or an optical characteristic.

11. The method of claim 1, wherein measuring at least one response characteristic of the resonator comprises measuring at least one of a velocity or a displacement of amplitude or phase of the resonator in at least one of a time domain or a frequency domain.

12. The method of claim 1, wherein comparing the at least one measured response characteristic to a rheological model comprises comparing at least one motion response characteristic of the resonator to at least one of a mathematical model or a computational model.

13. The method of claim 12, wherein the at least one of the mathematical model or the computational model relates a change in the at least one motion response characteristic to at least one of a deformation amplitude or a deformation rate induced in the fluid sample.

14. The method of claim 1, wherein actuating the resonator disposed in the volume that contains the fluid sample to operate the resonator in the fluid sample at the predetermined actuation scheme comprises actuating a mechanical oscillator disposed in the volume that contains the fluid sample to vibrate the mechanical oscillator in the fluid sample at a predetermined vibration protocol.

15. The method of claim 14, wherein measuring the at least one response characteristic of the resonator based on the operation of the resonator in the fluid sample comprises measuring at least one motion response characteristic of the mechanical oscillator based on a non-linear response of the mechanical oscillator in the fluid sample.

16. The method of claim 15, wherein comparing the at least one measured response characteristic to a rheological model that associates characteristics of the fluid sample to one or more rheological properties comprises comparing the at least one measured motion response characteristic to the rheological model that associates motion characteristics of the fluid sample to one or more rheological properties.

17. The method of claim 15, wherein measuring the at least one motion response characteristic of the mechanical oscillator comprises measuring the at least one motion response characteristic with the photodetector positioned to receive the reflected laser beam that originates with the laser beam source and reflects from the vibrating mechanical oscillator.

18. The method of claim 1, further comprising circulating the fluid sample into the volume during actuation of the resonator.

19. The method of claim 1, wherein determining one or more rheological properties of the fluid sample comprises iteratively determining the one or more rheological properties of the fluid sample with a numerical inversion or optimization protocol.

20. The method of claim 1, wherein the one or more rheological properties comprises at least one of a complex viscosity, a storage modulus, a loss modulus, an apparent viscosity, a flow index, or a consistency factor of the fluid sample.

21. The method of claim 1, wherein the rheological model comprises at least one of a Bingham Plastic model, a power law model, a Hershel-Bulkley model, or a Carreau model.

22. The method of claim 1, wherein the fluid sample comprises a non-Newtonian liquid.

23. The method of claim 22, wherein the non-Newtonian liquid comprises a hydrocarbon liquid, a completion liquid, or a petroleum-derived liquid.

* * * * *